United States Patent [19]

Baumann

[11] 4,281,115

[45] Jul. 28, 1981

[54] 3-DICYANOMETHYLIDENE-2,3-DIHYDROTHIOPHEN-1,1-DIOXIDE DERIVATIVES

[75] Inventor: Werner Baumann, Therwil, Switzerland

[73] Assignee: Sandoz Ltd., Basel, Switzerland

[21] Appl. No.: 60,745

[22] Filed: Jul. 25, 1979

[30] Foreign Application Priority Data

Jul. 28, 1978 [CH] Switzerland .................. 8151/78

[51] Int. Cl.$^3$ .................. C07D 333/52; C07D 409/06
[52] U.S. Cl. .................. 542/441; 542/449; 549/46; 549/53
[58] Field of Search .................. 549/53; 542/449, 441

[56] References Cited

U.S. PATENT DOCUMENTS

| | | | |
|---|---|---|---|
| 3,682,899 | 8/1972 | Nishio et al. | 542/441 |
| 3,716,531 | 2/1973 | Albrecht et al. | 549/53 |
| 4,127,667 | 11/1978 | Rovnyak | 542/449 |
| 4,128,647 | 12/1978 | Rovnyak | 542/449 |

FOREIGN PATENT DOCUMENTS 2042663  3/1972  Fed. Rep. of Germany.

*Primary Examiner*—Arthur P. Demers
*Attorney, Agent, or Firm*—Gerald D. Sharkin; Richard E. Vila; Thomas C. Doyle

[57] ABSTRACT

The present invention relates to disperse dyes containing a group of formula I,

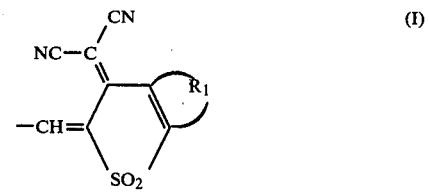

in which $R_1$ signifies the atoms necessary to complete an arylene radical, their production and intermediates therefor.

16 Claims, No Drawings

3-DICYANOMETHYLIDENE-2,3-DIHYDROTHIOPHEN-1,1-DIOXIDE DERIVATIVES

The present invention relates to disperse dyestuffs which are 3-dicyanomethylidene 2,3-dihydrothiophen 1,1-dioxide derivatives.

More particularly, the present invention provides disperse dyestuffs containing the group of formula I,

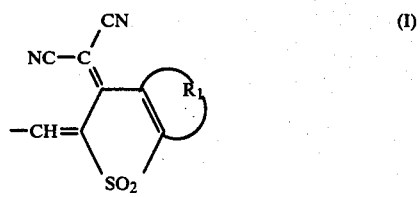

in which $R_1$ signifies the atoms necessary to complete an arylene radical.

Preferred dyestuffs are those in which the group of formula I is bound to a group of the benzene, indoline or hydroquinoline series.

More preferred dyestuffs are those of formula $I_a$,

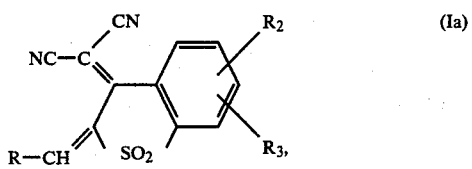

in which R is a group of formula (a) or (b),

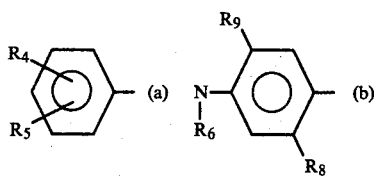

$R_2$ is hydrogen, chlorine, bromine, hydroxy, amino, $(C_{1-2})$alkyl, phenyl, $(C_{1-2})$alkoxy, phenoxy, cyano, nitro, $(C_{1-4})$alkylsulphonyl, aminosulphonyl, mono- or di-$(C_{1-4})$alkylaminosulphonyl, phenylaminosulphonyl, N-phenyl-N-$(C_{1-2})$alkylaminosulphonyl, alkoxy$(C_{1-6})$carbonyl, phenoxycarbonyl, aminocarbonyl, mono- or di$(C_{1-4})$alkylaminocarbonyl, phenylaminocarbonyl, N-phenyl-N-$(C_{1-2})$alkylaminocarbonyl, alkyl$(C_{1-6})$carbonyloxy, chloro- or bromo-$(C_{1-2})$alkylcarbonyloxy, alkoxy$(C_{1-6})$carbonyloxy, $(C_{1-2})$alkoxy$(C_{2-6})$alkoxycarbonyloxy, phenoxycarbonyloxy, $(C_{1-4})$alkylsulphonyloxy, phenylsulphonyloxy, alkyl$(C_{1-4})$carbonylamino, alkoxy$(C_{1-2})$alkoxy$(C_{2-4})$carbonylamino, chloro- or bromo-alkyl$(C_{1-2})$carbonylamino, alkoxy$(C_{1-4})$-carbonylamino, phenoxycarbonylamino, aminocarbonylamino, mono- or di$(C_{1-4})$alkylaminocarbonylamino, phenylaminocarbonylamino, N-phenyl-N-$(C_{1-2})$alkylaminocarbonylamino, benzoyloxy, naphthoyloxy, benzoylamino, di-$(C_{1-4})$alkylaminosulphonyloxy, mono- or di-$(C_{1-4})$alkylaminocarbonyloxy or phenylaminocarbonyloxy, $R_3$ is hydrogen, chlorine, bromine, $(C_{1-2})$-alkyl, $(C_{1-2})$alkoxy or alkoxy$(C_{1-4})$carbonyl, $R_4$ is hydroxyl, $(C_{1-4})$alkoxy or —$NR_6R_7$, $R_5$ is hydrogen, chlorine, bromine, hydroxyl, $(C_{1-4})$alkyl, $(C_{1-4})$alkoxy, phenoxy, alkyl$(C_{1-6})$carbonylamino, phenylcarbonylamino, alkoxy$(C_{1-4})$carbonylamino, alkyl$(C_{1-6})$carbonyloxy, phenylcarbonyloxy, naphthylcarbonyloxy, chloro- or bromoalkyl$(C_{1-2})$carbonyloxy, alkoxy$(C_{1-6})$-carbonyloxy, alkoxy$(C_{1-2})$alkoxy$(C_{2-6})$-carbonyloxy, phenoxycarbonyloxy $(C_{1-4})$-alkylsulphonyloxy, phenylsulphonyloxy, di-$(C_{1-4})$alkylaminosulphonyloxy, di$(C_{1-4})$alkylaminocarbonyloxy, $(C_{1-6})$alkylaminocarbonyloxy, phenyl, phenylaminocarbonyloxy or phenoxycarbonylamino each of $R_6$ and $R_7$, independently, is hydrogen, $(C_{1-12})$alkyl, benzyl, chloro- or bromobenzyl, $(C_{5-7})$cycloalkyl, allyl, or $(C_{2-12})$alkyl monosubstituted by chlorine, bromine, hydroxyl, $(C_{1-12})$alkoxy, $(C_{1-6})$alkoxy$(C_{2-6})$alkoxy, phenyl, phenyl$(C_{1-6})$alkoxy, phenoxy$(C_{2-6})$alkoxy, cyano, naphthoxy, alkoxy $(C_{1-3})$carbonyl, alkyl $(C_{1-15})$carbonyloxy, alkoxy$(C_{1-12})$carbonyloxy, benzoyloxy, phenylaminocarbonyloxy or phenoxy, the benzene nucleus of which phenoxy being unsubstituted or substituted by a total of up to three substituents selected from chlorine, bromine, methyl (max. 3 of each), $(C_{1-4})$alkoxy (max. 2 of these), $(C_{2-12})$alkyl and phenyl (max. 1 of each of these), $R_8$ is hydrogen, chlorine, bromine, $(C_{1-2})$ alkyl or $(C_{1-2})$alkoxy, and $R_9$ is —$CH_2CH_2$—, —$(CH_2)_3$—, —$C^*(CH_3)_2$—$CH_2$—$CH(CH_3)$— or —$C^*(CH_3)_2$—$CH$=$C(CH_3)$— where the carbon atom marked with the asterisk is attached to the N-atom.

Any alkyl groups or moieties in the molecule may be straight-chain or branched with the proviso that the molecule is free from acetal groupings e.g.

$$-O-\overset{|}{\underset{|}{C}}-O- \quad \text{and} \quad -N-\overset{|}{\underset{|}{C}}-O-.$$

$R_2$ is preferably $R_2'$, where $R_2'$ is hydrogen, chlorine, bromine, hydroxy, $(C_{1-2})$alkoxy, cyano, nitro, methyl, alkoxy$(C_{1-6})$carbonyl, phenoxycarbonyl, aminocarbonyl, mono- di-$(C_{1-4})$alkylaminocarbonyl, phenylaminocarbonyl, N-phenyl-N-$(C_{1-2})$alkylaminocarbonyl, alkyl$(C_{1-6})$carbonyloxy, benzoyloxy, alkoxy$(C_{1-6})$carbonyloxy or phenoxycarbonyloxy. More preferably, $R_2$ is $R_2''$, where $R_2''$ is hydrogen or in the 5'- or 6'-position, chlorine, bromine, methyl, methoxy or ethoxy. Most preferably $R_2$ is hydrogen or chlorine in the 6'-position.

$R_3$ is preferably hydrogen.

$R_4$ is preferably —$NR_6R_7$ bound to the 4-position.

$R_5$ is preferably $R_5'$, wherein $R_5'$ is hydrogen, methyl, methoxy or ethoxy in the 2-position.

$R_6$ is preferably $R_6'$, where $R_6'$ is $(C_{1-12})$alkyl, benzyl, chlorobenzyl, $(C_{5-7})$ (preferably $C_6$) cycloalkyl, allyl, or $(C_{2-12})$ alkyl mono substituted by chlorine, bromine, hydroxyl, $(C_{1-12})$alkoxy, phenyl, phenyl$(C_{1-6})$alkoxy, $(C_{1-6})$alkoxy$(C_{2-6})$alkoxy, phenoxy$(C_{2-6})$alkoxy, naphthoxy or phenoxy, the benzene nucleus of which phenoxy being unsubstituted or substituted by up to three substituents selected from the group consisting of chlorine, bromine, methyl (up to 3 of each of these), $(C_{1-4})$alkoxy (max. 2 of these), $(C_{2-12})$alkyl and phenyl (max. one of each of these).

$R_7$ is preferably $R_7'$ where $R_7'$ has one of the significances of $R_6'$.

$R_6$ is more preferably $R_6''$, where $R_6''$ is $(C_{1-12})$alkyl, benzyl or $(C_{2-12})$alkyl monosubstituted by $(C_{1-12})$alkoxy, phenyl, phenyl-$(C_{1-3})$alkoxy, $(C_{1-4})$alkoxy$(C_{2-4})$alkoxy, phenoxy$(C_{2-6})$alkoxy, naphthoxy or phenoxy, the benzene nucleus of which phenoxy is unsubstituted or substituted by up to three substituents selected from the group consisting of chloro, bromine, methyl (up to three of each of these), $(C_{1-2})$alkoxy (max. two of these), $(C_{2-8})$alkyl and phenyl (max. one of each of these). Most preferably $R_6$ is $(C_{2-8})$-alkyl or phenyl$(C_{1-3})$alkyl.

$R_7$ is preferably $R_7''$ where $R_7''$ has one of the significance of $R_6''$ with the proviso that at least one of $R_6''$ and $R_7''$ contains at least 4 carbon atoms. Most preferably $R_7$ is $(C_{4-12})$alkyl or phenyl$(C_{2-3})$alkyl.

$R_8$ is preferably $R_8'$ where $R_8'$ is hydrogen or methyl.

Thus, preferred compounds of formula $I_a$, are those in which $R_5$ is $R_5'$, $R_6$ is $R_6'$ and $R_7$ is $R_7'$.

More preferred compounds are those of formula $I_b$ and $I_c$.

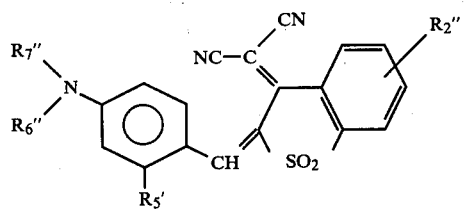

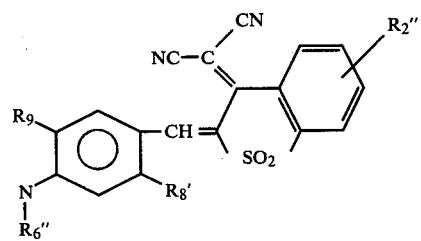

in which $R_2''$, $R_5''$, $R_6''$, $R_7''$, $R_8'$ and $R_9$ are as defined above,
especially those compounds of formula $I_b$ and $I_c$, in which $R_2''$ is hydrogen or chlorine in the 6-position and in which any phenoxy substituted-alkyl as $R_6''$ and/or $R_7''$ is an unsubstituted-phenoxyalkyl group.

Most preferred compounds of formula $I_b$ are those in which $R_6''$ is $(C_{2-8})$alkyl or phenyl$(C_{1-3})$alkyl and $R_7''$ is $(C_{4-12})$alkyl or phenyl $(C_{2-3})$alkyl.

Most preferred compounds of formula $I_c$ are those in which $R_6''$ is $(C_{2-8})$alkyl or phenyl$(C_{1-3})$alkyl. The compounds of formula $I_b$ are preferred.

The present invention further provides a process for the production of disperse dyes bearing a group of formula I, comprising condensing a compound of formula II,

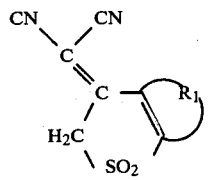

with an aldehyde or a functional derivative thereof.

The condensation reaction with the compound of formula II may be carried out under Knoevenagel condensation reaction conditions.

The condensation reaction is suitably effected in an inert organic solvent e.g. alcohols, especially ethanol, n-propanol; benzene, toluene; chlorobenzenes; chloroform; dimethylformamide; N-methylpyrrolidone; dimethylsulphoxide; sulpholane; acetonitrile etc.

Suitable reaction temperatures, when using an aldehyde or a functional derivative are from 20° to 150° C. With aldehyde the temperature is preferably from 30° to 100° C. It is advantageous to employ a catalyst, especially an organic base such as pyridine, piperidine or a piperidine/glacial acetic acid mixture. If the aldehyde is one which has been formed by the Vilsmeier Reaction, it is not necessary to separate the latter as the condensation reaction may be effected in the same reaction vessel, i.e. using the Vilsmeier Complex. If this is the case then the reaction is preferably conducted at a temperature from 0° and 100° C., more preferably from 20° to 80° C. Suitable functional derivatives of aldehydes include Schiff bases, acetals, sulphite addition products, oximes and hydrazones. Preferably, the reaction is carried out using an aldehyde or the Vilsmeier complex.

The compounds of formula II and their production also from part of the present invention.

The process for the production of the compounds of formula II comprises condensing a compound of formula III,

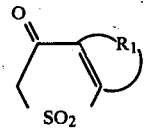

with malonic acid dinitrile.

The condensation reaction of the compound of formula III with malonic acid dinitrile is effected in accordance with known methods. e.g. Knoevenagel reaction condition as described above. Suitable temperatures are from 20° and 105° C., preferably 50°–120° C.

The compounds of formula III are either known or may be prepared in accordance with known methods from available starting materials.

The disperse dyestuffs according to the invention may be made up into dyeing preparations in accordance with known methods, for example by grinding in the presence of dispersing agents and/or fillers. Aqueous dispersions of such dyestuff preparation may be used for exhaust dyeing padding or printing textiles consisting of or comprising synthetic or semi-synthetic, hydrophobic, high-molecular organic materials. Especially preferred substrates include linear, aromatic polyesters, cellulose 2½ acetate, cellulose triacetate and synthetic polyamides.

Dyeing and printing may be effected in accordance with known methods, for example as described in French Pat. No. 1,445,371. The dyestuffs of the present invention are also suitable for dyeing by the well-known solvent dyeing processes.

The dyestuffs of the present invention give exceptionally brilliant dyeings. Furthermore the dyestuffs have high dyeing strength and thus give good deep dyeings.

The following Examples further serve to illustrate the invention. In the Examples all parts are by weight and the temperatures are given in degrees Centigrade.

EXAMPLE 1

(a) 20 Parts 3-oxo-2,3-dihydro-1-benzothiophene-1,1-dioxide, 8 parts malonic acid dinitrile and 0.2 parts of a mixture (1:5) of piperidine and glacial acetic acid are dissolved in 250 parts anhydrous ethanol and heated to 60° for 6 hours with stirring. A further 4 parts of malonic acid dinitrile are added and the mixture is stirred further for 16 hours at 60°. Subsequently, the mixture is cooled to 5° and the product of formula

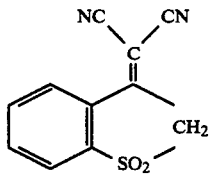

is filtered, washed with ice-cold ethanol and dried in vacuo.

(b) 12 Parts 3-N,N-di-n-hexyl-toluidine are dissolved in 50 parts dry dimethylformamide, reacted with 7 parts phosphorousoxychloride with cooling and subsequently heated at 60° for 4 hours. The cooled solution is added dropwise at room temperature with stirring to a suspension of 10 parts of the product obtained as described under (a) above and 15 parts anhydrous sodium acetate in 200 parts absolute alcohol. The mixture is stirred over-night at room temperature and the precipitated dye of formula

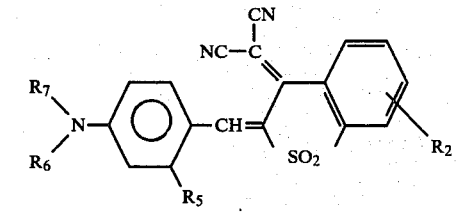

is filtered, washed with ice-cold absolute alcohol, slurried in 500 parts ice water, filtered again, washed with ice-cold water and dried in vacuo.

In analogy with the procedure described above the dyestuffs of the following Tables 1 and 2 may be prepared. The dyestuffs of Table 1 correspond to the formula

The starting materials of formula II of Examples 65 to 92 are made in analogy with the procedure described in Example 1(a).

TABLE 1

| Example No. | $R_2$ | $R_5$ | $R_6$ | $R_7$ |
|---|---|---|---|---|
| 2 | H | —$CH_3$ | —$C_2H_5$ | —$(CH_2)_5CH_3$ |
| 3 | H | " | " | —$(CH_2)_7CH_3$ |
| 4 | H | " | " | —$(CH_2)_9CH_3$ |
| 5 | H | " | " | —$(CH_2)_{11}CH_3$ |
| 6 | H | " | —$(CH_2)_3CH_3$ | —$(CH_2)_3CH_3$ |
| 7 | H | " | —$CH_2CH_2CH(CH_3)_2$ | —$CH_2CH_2CH(CH_3)_2$ |
| 8 | H | " | —$(CH_2)_7CH_3$ | " |
| 9 | H | " | " | —$(CH_2)_7CH_3$ |
| 10 | H | " | —$CH_2$—$C_6H_5$ | " |
| 11 | H | " | —$CH_2CH_2$—$C_6H_5$ | " |
| 12 | H | " | —$(CH_2)_3$—$C_6H_5$ | " |
| 13 | H | " | " | —$(CH_2)_3$—$C_6H_5$ |
| 14 | H | " | —$CH_2CH_2$—$C_6H_5$ | —$CH_2CH_2$—$C_6H_5$ |
| 15 | H | " | " | —$(CH_2)_3CH_3$ |
| 16 | H | " | —$CH_2$—$C_6H_5$ | " |
| 17 | H | " | —$(CH_2)_5CH_3$ | —$CH_2CH_2$—$OCH_3$ |
| 18 | H | " | —$(CH_2)_3CH_3$ | —$CH_2CH_2$—O—$C_2H_5$ |
| 19 | H | " | —$C_2H_5$ | —$CH_2CH_2$—O—$(CH_2)_3CH_3$ |
| 20 | H | " | " | —$CH_2CH_2$—O—$(CH_2)_7$—$CH_3$ |
| 21 | H | " | " | —$CH_2CH_2$—O—$(CH_2)_{11}CH_3$ |
| 22 | H | " | " | —$CH_2CH_2$—O—$CH_2$—$C_6H_5$ |
| 23 | H | " | " | —$CH_2CH_2$—O—$(CH_2)_3$—$C_6H_5$ |
| 24 | H | " | " | —$CH_2CH_2$—O—$(CH_2)_4$—$OCH_3$ |
| 25 | H | " | " | —$CH_2CH_2$—O—$(CH_2)_6$—$OCH_3$ |
| 26 | H | " | " | —$CH_2CH_2$—O—$CH_2CH_2$—O—$(CH_2)_3CH_3$ |
| 27 | H | " | " | —$CH_2CH_2$—O—$CH_2CH_2$—O—$(CH_2)_5CH_3$ |
| 28 | H | " | " | —$CH_2CH_2$—O—$CH_2CH_2$—O—$C_6H_5$ |
| 29 | H | " | " | —$CH_2CH_2$—O—$(CH_2)_6$—O—$C_6H_5$ |
| 30 | H | " | " | —$(CH_2)_4$—O—$C_6H_5$ |
| 31 | H | —$CH_3$ | —$C_2H_5$ | —$(CH_2)_5$—O—$C_6H_5$ |
| 32 | H | " | " | —$(CH_2)_6$—O—$C_6H_5$ |
| 33 | H | " | " | —$(CH_2)_{10}$—O—$C_6H_5$ |
| 34 | H | " | " | —$(CH_2)_{12}$—O—$C_6H_5$ |
| 35 | H | " | —$(CH_2)_3CH_3$ | —$CH_2CH_2$—O—⟨C_6H_4⟩—$CH_3$ |

TABLE 1-continued
| Example No. | R₂ | R₅ | R₆ | R₇ |
|---|---|---|---|---|
| 36 | H | " | " | 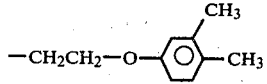 |
| 37 | H | " | " | 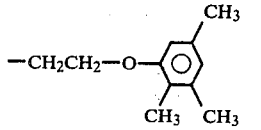 |
| 38 | H | " | " | 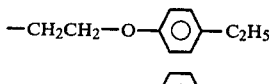 |
| 39 | H | " | —C₂H₅ | 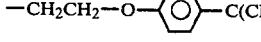 |
| 40 | H | " | " | 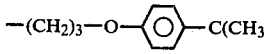 |
| 41 | H | " | " | 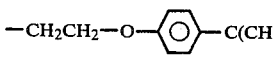 |
| 42 | H | " | " |  |
| 43 | H | " | " |  |
| 44 | H | " | " | 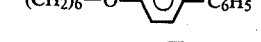 |
| 45 | H | " | " | 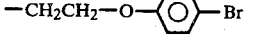 |
| 46 | H | " | " | 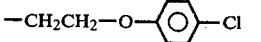 |
| 47 | H | " | " | 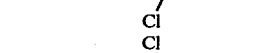 |
| 48 | H | " | " |  |
| 49 | H | " | —(CH₂)₃CH₃ |  |
| 50 | H | " | " |  |
| 51 | H | " | " | 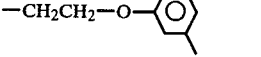 |
| 52 | H | —CH₃ | —C₂H₅ |  |
| 53 | H | " | —(CH₂)₃CH₃ | 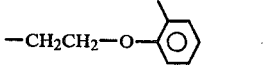 |
| 54 | H | " | " |  |
| 55 | H | " | " | Cyclohexyl |
| 56 | H | " | —(CH₂)₅CH₃ | —CH₂—CH=CH₂ |

TABLE 1-continued

| Example No. | R₂ | R₅ | R₆ | R₇ |
|---|---|---|---|---|
| 57 | H | " | —(CH₂)₇CH₃ | —CH₂CH₂—Cl |
| 58 | H | " | " | —CH₂CH₂—Br |
| 59 | H | " | " | —CH₂CH₂—OH |
| 60 | H | " | —C₂H₅ | —CH₂CH₂—O—CH(CH₂)₂CH₃ / CH₂CH₂—C₆H₅ |
| 61 | H | " | —CH₃ | —(CH₂)₁₁CH₃ |
| 62 | H | H | —C₂H₅ | —(CH₂)₉CH₃ |
| 63 | H | —OCH₃ | —(CH₂)₅CH₃ | —(CH₂)₅CH₃ |
| 64 | H | —OC₂H₅ | " | " |
| 65 | 6'-Cl | —CH₃ | —C₂H₅ | —C₂H₅ |
| 66 | " | " | —(CH₂)₃CH₃ | —(CH₂)₃CH₃ |
| 67 | 5'-Cl | " | " | " |
| 68 | 6'-Br | " | " | " |
| 69 | 5'-CH₃ | " | " | " |
| 70 | 6'-CH₃ | " | " | " |
| 71 | 5'-OH | " | " | " |
| 72 | 5'-OCH₃ | " | " | " |
| 73 | 5'-OC₂H₅ | " | " | " |
| 74 | 5'-CN | " | " | " |
| 75 | 5'-NO₂ | " | " | " |
| 76 | 6'-COOCH₃ | " | " | " |
| 77 | 6'-COO(CH₂)₅CH₃ | " | " | " |
| 78 | 6'-COOC₆H₅ | " | " | " |
| 79 | 6'-CONH₂ | " | " | " |
| 80 | 6'-CONH(CH₂)₃CH₃ | " | " | " |
| 81 | 6'-CON(CH₃)₂ | " | " | " |
| 82 | 6'-CONHC₆H₅ | " | " | " |
| 83 | 6'-CON(CH₃)C₆H₅ | " | " | " |
| 84 | 6'-CON(C₂H₅)C₆H₅ | " | " | " |
| 85 | 5'-OCOCH₃ | " | " | " |
| 86 | 5'-OCOC₂H₅ | " | " | " |
| 87 | 5'-OCO(CH₂)₅CH₃ | " | " | " |
| 88 | 5'-OCOC₆H₅ | " | " | " |
| 89 | 5'-O—CO—OCH₃ | " | " | " |
| 90 | 5'-O—CO—OC₂H₅ | " | " | " |
| 91 | 5'-O—CO—O(CH₂)₅CH₃ | " | " | " |
| 92 | 5'-O—CO—OC₆H₅ | " | " | " |

TABLE 2

The dyestuffs of this Table correspond to the formula

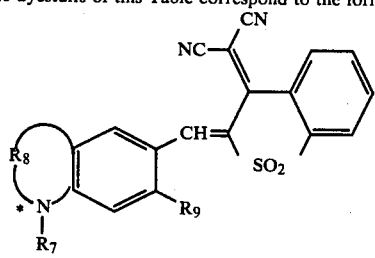

and give blue dyeings on polyester fibres.

| Example No. | R₇ | R₉ | R₈ |
|---|---|---|---|
| 93 | —(CH₂)₅CH₃ | —CH₂CH₂— | H |
| 94 | —(CH₂)₉CH₃ | " | H |
| 95 | —(CH₂)₅CH₃ | —(CH₂)₃— | H |
| 96 | —(CH₂)₇CH₃ | " | H |
| 97 | —(CH₂)₅CH₃ | *—C(CH₃)₂—CH₂—CH(CH₃)— | H |
| 98 | " | " | —CH₃ |
| 99 | " | *—C(CH₃)₂—CH=C(CH₃)— | " |
| 100 | —(CH₂)₃CH₃ | " | H |

Application Example 7 parts of the dyestuff obtained by Example 1 are ground with 13 parts sodiumligninsulphonate, 25 parts water and 100 parts silica quartz beads until the diameter of the dyestuff particles are less than 1μ. The suspension is filtered to separate the silica quartz beads and is dried under mild conditions. 1 Part of the so-obtained dyestuff preparation is stirred with 4000 parts water at 60°, which water is buffered to pH 5. Using this dyebath 100 parts polyester fabric are dyed at 98° for 1 hour with the addition of ortho-phenylphenol. After cooling, rinsing, soaping, rinsing again and drying, a exceptionally brilliant even blue dyeing with good fastnesses is obtained.

In analogy to the procedure described above the dyestuff of Examples 2–100 may be used to give brilliant blue dyeings on polyester fibres.

What we claim is:

1. A disperse dyestuff of the formula

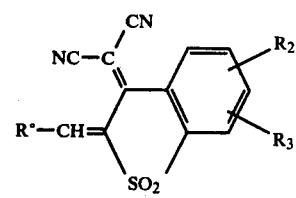

in which

R° is a group of the benzene, indoline or hydroquinoline series,

R₂ is hydrogen, chlorine, bromine, hydroxy, amino, (C₁₋₂)alkyl, phenyl, (C₁₋₂)alkoxy, phenoxy, cyano, nitro, (C₁₋₄)alkylsulphonyl, aminosulphonyl, mono- or di-(C₁₋₄)alkylaminosulphonyl, phenylaminosulphonyl, N-phenyl-N-$(C_{1-2})$alkylaminosulphonyl, alkoxy$(C_{1-6})$ carbonyl, phenoxycarbonyl, aminocarbonyl, mono- or di-$(C_{1-4})$alkylaminocarbonyl, phenylaminocarbonyl, N-phenyl-N-$(C_{1-2})$alkylaminocarbonyl, alkyl$(C_{1-6})$carbonyloxy, chloro- or bromo-$(C_{1-2})$alkylcarbonyloxy, $(C_{1-2})$alkoxy$(C_{2-6})$alkoxy carbonyloxy, phenoxycarbonyloxy, $(C_{1-4})$alkylsulphonyloxy, phenylsulphonyloxy, alkyl$(C_{1-4})$carbonylamino, alkoxy$(C_{1-2})$alkoxy$(C_{2-4})$carbonylamino, chloro- or bromo-alkyl$(C_{1-2})$carbonylamino, alkoxy$(C_{1-4})$-carbonylamino, phenoxycarbonylamino, aminocarbonylamino, mono- or di-$(C_{1-4})$-alkylaminocarbonylamino, phenylaminocarbonylamino, N-phenyl-N-$(C_{1-2})$alkylaminocarbonylamino, benzoyloxy, naphthoyloxy, benzoylamino, di-$(C_{1-4})$alkylaminosulphonyloxy, mono- or di-$(C_{1-4})$alkylaminocarbonyloxy or phenylaminocarbonyloxy, and $R_3$ is hydrogen, chlorine, bromine, $(C_{1-2})$alkyl, $(C_{1-2})$alkoxy or alkoxy$(C_{1-4})$carbonyl.

2. A compound of formula $I_a$,

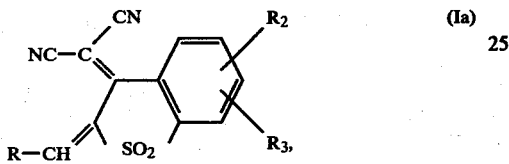

in which R is a group of formula (a) or (b),

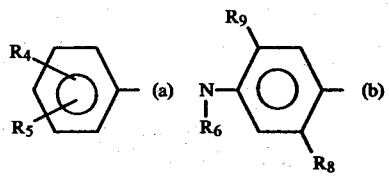

$R_2$ is hydrogen, chlorine, bromine, hydroxy, amino, $(C_{1-2})$alkyl, phenyl, $(C_{1-2})$alkoxy, phenoxy, cyano, nitro, $(C_{1-4})$alkylsulphonyl, aminosulphonyl, mono- or di-$(C_{1-4})$alkylaminosulphonyl, phenylaminosulphonyl, N-phenyl-N-$(C_{1-2})$alkylaminosulphonyl, alkoxy$(C_{1-6})$ carbonyl, phenoxycarbonyl, aminocarbonyl, mono- or di$(C_{1-2})$alkylaminocarbonyl, phenylaminocarbonyl, N-phenyl-N-$(C_{1-2})$alkylaminocarbonyl, alkyl$(C_{1-6})$carbonyloxy, chloro- or bromo-$(C_{1-2})$alkylcarbonyloxy, alkoxy$(C_{1-6})$carbonyloxy, $(C_{1-2})$alkoxy$(C_{2-6})$alkoxy carbonyloxy, phenoxycarbonyloxy, $(C_{1-4})$ alkylsulphonyloxy, phenylsulphonyloxy, alkyl$(C_{1-4})$carbonylamino, alkoxy$(C_{1-2})$alkoxy$(C_{2-4})$carbonylamino, chloro- or bromo-alkyl$(C_{1-2})$carbonylamino, alkoxy$(C_{1-4})$- carbonylamino, phenoxycarbonylamino, aminocarbonylamino, mono- or di$(C_{1-4})$alkylaminocarbonylamino, phenylaminocarbonylamino, N-phenyl-N-$(C_{1-2})$alkylaminocarbonylamino, benzoyloxy, napthoyloxy, benzoylamino, di-$(C_{1-4})$alkylaminosulphonyloxy, mono- or di-$(C_{1-4})$alkylaminocarbonyloxy or phenylaminocarbonyloxy, $R_3$ is hydrogen, chlorine, bromine, $(C_{1-2})$-alkyl, $(C_{1-2})$alkoxy or alkoxy$(C_{1-4})$carbonyl, $R_4$ is hydroxyl, $(C_{1-4})$alkoxy or —$NR_6R_7$, $R_5$ is hydrogen, chlorine, bromine, hydroxyl, $(C_{1-4}$(alkyl, $(C_{1-4})$alkoxy, phenoxy, alkyl$(C_{1-6})$carbonylamino, phenylcarbonylamino, alkoxy$(C_{1-4})$carbonylamino, alkyl$(C_{1-6})$carbonyloxy, phenylcarbonyloxy, naphthylcarbonyloxy, chloro- or bromoalkyl$(C_{1-2})$carbonyloxy, alkoxy$(C_{1-6})$carbonyloxy, alkoxy$(C_{1-2})$alkoxy$(C_{2-6})$-carbonyloxy, phenoxycarbonyloxy, $(C_{1-4})$-alkylsulphonyloxy, phenylsulphonyloxy, di-$(C_{1-4})$alkylaminosulphonyloxy, di$(C_{1-4})$alkylaminocarbonyloxy, $(C_{1-6})$alkylaminocarbonyloxy, phenyl, phenylaminocarbonyloxy or phenoxycarbonylamino each of $R_6$ and $R_7$, independently, is hydrogen, $(C_{1-12})$alkyl, benzyl, chloro- or bromobenzyl, $(C_{5-7})$cycloalkyl, allyl, or $(C_{2-12})$alkyl monosubstituted by chlorine, bromine, hydroxyl, $(C_{1-12})$alkoxy, $(C_{1-6})$alkoxy$(C_{2-6})$alkoxy, phenyl, phenyl$(C_{1-6})$alkoxy, phenoxy$(C_{2-6})$alkoxy, cyano, naphthoxy, alkoxy $(C_{1-3})$carbonyl, alkyl $(C_{1-15})$ carbonyloxy, alkoxy$(C_{1-12})$carbonyloxy, benzoyloxy, phenylaminocarbonyloxy or phenoxy, the benzene nucleus of which phenoxy being unsubstituted or substituted by a total of up to three substituents selected from chlorine, bromine, methyl (max. 3 of each), $(C_{1-4})$alkoxy (max. 2 of these), $(C_{2-12})$alkyl and phenyl (max. 1 of each of these), $R_8$ is hydrogen, chlorine, bromine, $(C_{1-2})$ alkyl or $(C_{1-2})$alkoxy, and $R_9$ is —$CH_2CH_2$—, —$(CH_2)_3$—, —$C*(CH_3)_2$—$CH_2$—$CH(CH_3)$— or —$C*(CH_3)_2$—$CH$=$C(CH_3)$— where the carbon atom marked with the asterisk is attached to the N-atom.

3. A compound according to claim 2 in which R is a group of formula (a), $R_4$ is —$NR_6R_7$ in the 4-position, $R_5$ is $R_5'$, where $R_5'$ is hydrogen or methyl, methoxy or ethoxy in the 2-position. $R_6$ is $R_6'$, where $R_6'$ is $(C_{1-12})$alkyl, benzyl, chlorobenzyl, $(C_{5-7})$ cycloalkyl, allyl, or $(C_{2-12})$alkyl mono substituted by chlorine, bromine, hydroxyl, $(C_{1-12})$-alkoxy, phenyl, phenyl$(C_{1-6})$alkoxy, $(C_{1-6})$alkoxy$(C_{2-6})$-alkoxy, phenoxy$(C_{2-6})$alkoxy, naphthoxy or phenoxy, the benzene nucleus of which phenoxy being unsubstituted or substituted by up to three substituents selected from the group consisting of chlorine, bromine, methyl (up to 3 of each of these), $(C_{1-4})$alkoxy (max. 2 of these), $(C_{2-12})$alkyl and phenyl (max. one each of these), and $R_7$ is $R_7'$, where $R_7'$ has one of the significances of $R_6'$.

4. A compound according to claim 3, of formula $I_b$,

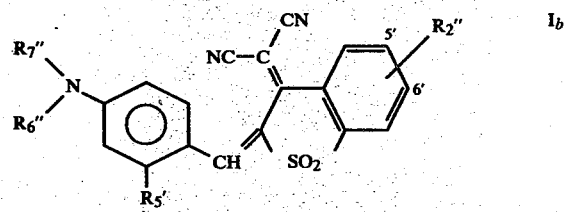

in which
$R_2''$ is hydrogen or, in the 5'- or 6'-position, chlorine, bromine, methyl, methoxy or ethoxy,
and each of
$R_6''$ and $R_7''$, independently is $(C_{1-12})$alkyl, benzyl, or $(C_{2-12})$alkyl monosubstituted by $(C_{1-12})$alkoxy, phenyl, phenyl$(C_{1-3})$-alkoxy, $(C_{1-4})$alkoxy$(C_{2-4})$alkoxy, phenoxy$(C_{2-6})$alkoxy, naphthoxy or phenoxy, the benzene nucleus of which phenoxy is unsubstituted or substituted by up to three substituents selected from the group consisting of chloro, bromine, methyl (up to three of each of these), ($C_{1-2}$)alkoxy (max. two of these), ($C_{2-8}$)-alkyl and phenyl (max. one of each of these).

5. A compound according to claim 2 of formula $I_c$

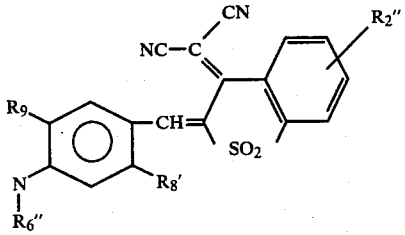

in which
$R_8'$ is hydrogen or methyl
$R_2''$ is hydrogen or, in the 5'- or 6'-position, chlorine, bromine, methyl, methoxy or ethoxy,
and $R_6''$ is ($C_{1-12}$)alkyl, benzyl, or ($C_{2-12}$)alkyl monosubstituted by ($C_{1-12}$)alkoxy, phenyl, phenyl($C_{1-3}$)alkoxy, ($C_{1-4}$)alkoxy($C_{2-4}$)alkoxy, phenoxy($C_{2-6}$)alkoxy, naphthoxy or phenoxy, the benzene nucleus of which phenoxy is unsubstituted or substituted by up to three substituents selected from the group consisting of chloro, bromine, methyl (up to three of each of these), ($C_{1-12}$)alkoxy (max. two of these), ($C_{2-8}$)-alkyl and phenyl (max. one of each of these).

6. A compound according to claim 2 of formula

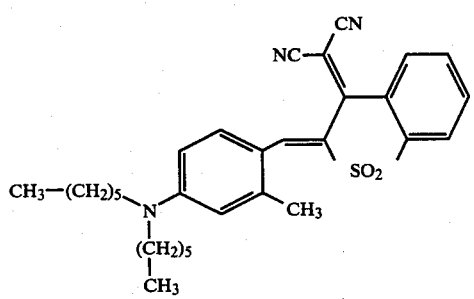

7. A compound according to claim 2 in which R is a group of formula (a).

8. A compound according to claim 2 in which R is a group of formula (b).

9. A compound according to claim 4 wherein $R_6''$ is ($C_{2-8}$)alkyl or phenyl($C_{1-3}$)alkyl and $R_7''$ is ($C_{4-12}$)alkyl or phenyl($C_{2-3}$)alkyl.

10. A compound according to claim 5 wherein $R_6''$ is ($C_{2-8}$)alkyl or phenyl($C_{1-3}$)alkyl.

11. A compound according to claim 3 wherein $R_2$ is $R_2'$ wherein $R_2'$ is hydrogen, chlorine, bromine hydroxy, ($C_{1-2}$) alkoxy, cyano, nitro, methyl, alkoxy ($C_{1-6}$) carbonyl, phenoxycarbonyl, aminocarbonyl, mono-or di-($C_{1-4}$) alkylaminocarbonyl, phenylaminocarbonyl, N-phenyl-N-($C_{1-2}$) alkylamino-carbonyl, alkyl ($C_{1-6}$) carbonyloxy, benzoyloxy, alkoxy ($C_{1-6}$) carbonyloxy or phenoxycarbonyloxy.

12. A compound according to claim 11 wherein $R_3$ is hydrogen.

13. A compound of formula II,

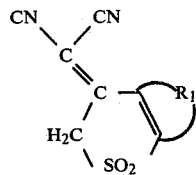

in which $R_1$ signifies the atoms necessary to complete an ortho, arylene radical.

14. A compound according to claim 13 wherein $R_1$ specifies the atoms necessary to complete an ortho-phenylene or substituted ortho-phenylene radical.

15. A compound according to claim 14 of the formula

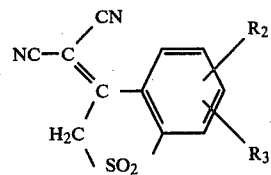

in which
$R_2$ is hydrogen, chlorine, bromine, hydroxy, amino, ($C_{1-2}$)alkyl, phenyl, ($C_{1-2}$)alkoxy, phenoxy, cyano, nitro, ($C_{1-4}$)alkylsulphonyl, aminosulphonyl, mono- or di-($C_{1-4}$)alkylaminosulphonyl, phenylaminosulphonyl, N-phenyl-N-($C_{1-2}$)alkylaminosulphonyl, alkoxy($C_{1-6}$) carbonyl, phenoxycarbonyl, aminocarbonyl, mono- or di($C_{1-4}$)alkylaminocarbonyl, phenylaminocarbonyl, N-phenyl-N-($C_{1-2}$)alkylaminocarbonyl, alkyl($C_{1-6}$)carbonyloxy, chloro- or bromo-($C_{1-2}$)alkylcarbonyloxy, ($C_{1-2}$)alkoxy($C_{2-6}$)alkoxy carbonyloxy, phenoxycarbonyloxy, ($C_{1-4}$)alkylsulphonyloxy, phenylsulphonyloxy, alkyl($C_{1-4}$)carbonylamino, alkoxy($C_{1-2}$)alkoxy($C_{2-4}$)carbonylamino, chloro- or bromo-alkyl($C_{1-2}$)carbonylamino, alkoxy($C_{1-4}$)-carbonylamino, phenoxycarbonylamino, aminocarbonylamino, mono- or di-($C_{1-4}$)-alkylaminocarbonylamino, phenylaminocarbonylamino, N-phenyl-N-($C_{1-2}$)alkylaminocarbonylamino, benzoyloxy, naphthoyloxy, benzoylamino, di-($C_{1-4}$)alkylaminosulphonyloxy, mono- or di-($C_{1-4}$)alkylaminocarbonyloxy or phenylaminocarbonyloxy,
and $R_3$ is hydrogen, chlorine, bromine, ($C_{1-2}$)alkyl, ($C_{1-2}$)alkoxy or alkoxy($C_{1-4}$)carbonyl.

16. A compound according to claim 15 wherein $R_2$ is $R_2'$ wherein $R_2'$ is hydrogen, chlorine, bromine, hydroxy, ($C_{1-2}$)alkoxy, cyano, nitro, methyl, alkoxy ($C_{1-6}$)carbonyl, phenoxycarbonyl, aminocarbonyl, mono- or di-($C_{1-4}$) alkylaminocarbonyl, phenylaminocarbonyl, N-phenyl-N-($C_{1-2}$) alkylamino carbonyl, alkyl ($C_{1-6}$)carbonyloxy, benzoyloxy, alkoxy ($C_{1-6}$)carbonyloxy or phenoxycarbonyloxy and $R_3$ is hydrogen.

* * * * *

UNITED STATES PATENT AND TRADEMARK OFFICE
CERTIFICATE OF CORRECTION

PATENT NO. : 4,281,115
DATED : July 28, 1981
INVENTOR(S) : Werner Baumann

It is certified that error appears in the above—identified patent and that said Letters Patent is hereby corrected as shown below:

Column 1, lines 35-42 and column 11, lines 32-40; change formula (b) to

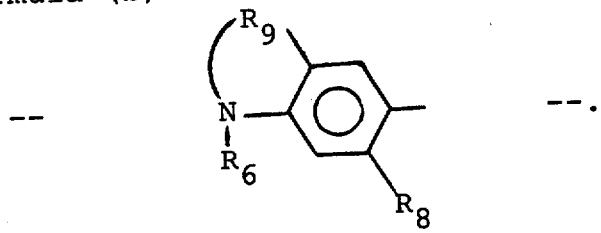

Column 2, line 43; after "mono-" insert --or--.

Column 3, lines 30-40 and column 13, lines 6-15; change the left-hand portion of formula $I_c$ to

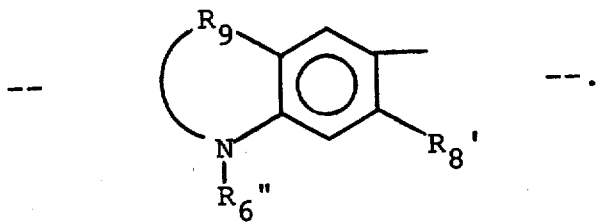

UNITED STATES PATENT AND TRADEMARK OFFICE
CERTIFICATE OF CORRECTION

PATENT NO. : 4,281,115
DATED : July 28, 1981
INVENTOR(S) : Werner Baumann

It is certified that error appears in the above—identified patent and that said Letters Patent is hereby corrected as shown below:

Column 3, the first line below the formulae; change " $R_5$ " " to -- $R_5'$ --.

Column 9, Table 2 in the formula; " $R_8$ " should be -- $R_9$ -- and " $R_9$ " should be -- $R_8$ --.

Signed and Sealed this

First Day of June 1982

[SEAL]

Attest:

GERALD J. MOSSINGHOFF

Attesting Officer    Commissioner of Patents and Trademarks